(12) United States Patent
Saeki et al.

(10) Patent No.: US 7,745,154 B2
(45) Date of Patent: Jun. 29, 2010

(54) PREVENTIVES/REMEDIES FOR MYELOMA TUMOR AND METHOD OF DIAGNOSING THE SAME

(75) Inventors: Yukihiko Saeki, Osaka (JP); Hideyuki Kobayashi, Saitama (JP); Yuichiro Tabunoki, Tokyo (JP)

(73) Assignee: Kowa Co., Ltd., Nagoya-shi (JP)

( * ) Notice: Subject to any disclaimer, the term of this patent is extended or adjusted under 35 U.S.C. 154(b) by 983 days.

(21) Appl. No.: 10/508,150

(22) PCT Filed: Mar. 19, 2003

(86) PCT No.: PCT/JP03/03314

§ 371 (c)(1),
(2), (4) Date: Sep. 17, 2004

(87) PCT Pub. No.: WO03/077948

PCT Pub. Date: Sep. 25, 2003

(65) Prior Publication Data

US 2005/0250162 A1 Nov. 10, 2005

(30) Foreign Application Priority Data

Mar. 19, 2002 (JP) .............................. 2002-076501

(51) Int. Cl.
*G01N 33/574* (2006.01)
*C12Q 1/00* (2006.01)
(52) U.S. Cl. ......................................... 435/7.23; 514/2
(58) Field of Classification Search .................... 514/2, 514/44, 17, 384, 327
See application file for complete search history.

(56) References Cited

U.S. PATENT DOCUMENTS

2005/0119204 A1* 6/2005 Chabas et al. ............... 514/44

OTHER PUBLICATIONS

Bautista et al, "Quantification of Osteopontin in Human Plasma with an Elisa: Basal levels in Pre- and Postmenopausal Women", Clinical Biochemistry, vol. 29, Jun. 1996,p. 231-239.*
McPhaden et al "Plasma osteopontin levels in multiple myeloma", Blood,1994, vol. 84, No. 10 ,suppl. 1,p. 172A.*
On-line Medical Dictionary, "drug screening assays, antitumour", www.cancerweb.ncl.ac.uk/cgi-bin/omd?drug+screening+assays,+antitumour , Dec. 12, 1998 p. 1.*
Hussein et al "Multiple myeloma: present and future", Current opinion in oncology, vol. 14(1), Jan. 2002, pp. 31-35.*
Okada et al, American Journal of Physiology-Renal Physiology 2000, vol. 278:F110-F121.*
Fonesca, et al., British Journal of Haematology 2000, vol. 109, p. 24-29.*
Weber, Georg F. "The metastasis gene osteopontin: a candidate target for cancer therapy", Biochimica et Biophysica Acta 1552, pp. 61-85 2001.
Kato, Yoichiro et al. "Osteopontin Expression May Be Induced by c-Src in Papillary Thyroid Carcinoma", Acta Histochem. Cytochem, 34(3), pp. 193-199 2001.
Ue, Teruyoshi et al. "Hito Igan Saibo ni okeru osteopontin to CD44 no Kyotsu Hatsugen", Proceedings of Japanese Research Society for Gastroenterological Carcinogenesis, vol. 9, pp. 299-300, with English translation 1997.
Tuck, Alan B. et al. "Osteopontin Expression in a Group of Lymphnode Negative Breast Cancer Patients", Int. J. Cancer(Pred. Oncol.), vol. 79 pp. 502-508 1998.
Ue, Teruyoshi et al., "Co-Expression of Osteopontin and CD44v9 in Gastric Cancer", Int. J. Cancer (Pred. Oncol.). vol. 79, pp. 127-132 1998.
Takahashi, Kazuhisa et al. "Hai Shikkan to Osteopontin", Respiration Research, vol. 21, No. 7, pp. 634-639, with Partial English translation Jul. 15, 2002.
Proceedings of the American Association for Cancer Research, vol. 36, Mar. 1995 p. 222, Bautista et al.
Diosdado S. Bautista, et al.,"Inhibition of Arg-Gly-Asp (RGD)-mediated Cell Adhesion to Osteopontin by a Monoclonal Antibody against Osteopontin", The Journal of Biological Chemistry, vol. 269, No. 37, Issue of Sep. 16, 1994, pp. 23280-23285.

* cited by examiner

*Primary Examiner*—Jon P Weber
*Assistant Examiner*—Laura Schuberg
(74) *Attorney, Agent, or Firm*—Oblon, Spivak, McClelland, Maier & Neustadt, L.L.P.

(57) ABSTRACT

The present invention provides a preventive or therapeutic drug for a myeloma tumor and osteoclastic bone loss associating therewith, the drug containing as an active ingredient an osteopontin-production regulator or inhibitor; a screening method for a preventive or therapeutic drug for a myeloma tumor, characterized by determining osteopontin production regulatory or inhibitory effect; as well as a diagnostic kit for a myeloma tumor, characterized by including a reagent for measuring blood osteopontin level, and a diagnostic method.

10 Claims, 8 Drawing Sheets

Multiple myeloma-derived bone marrow cells    Control group (MGUS)

```
                        SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
ggactccatt gactcgaacg                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
taatctggac tgcttgtggc                                                  20

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
aattaccaca acccctacaa ac                                               22

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
caactctgca acatcttcct c                                                21
```

PREVENTIVES/REMEDIES FOR MYELOMA TUMOR AND METHOD OF DIAGNOSING THE SAME

TECHNICAL FIELD

The present invention relates to preventive or therapeutic agents (drugs) for myeloma tumors, a screening method therefor, and a diagnostic method for myeloma tumors.

BACKGROUND ART

In drug therapy for cancer, chemotherapeutics are frequently employed. Most such chemotherapeutics exhibit strong side effects in addition to anti-cancer effect. When adverse side effects are developed, in some cases administration of the cancer chemotherapeutic is inevitably restricted. In such a case, only insufficient effect of the drug may be obtained, or no effect at all may be obtained. In particular, in therapy for myeloma tumor, which is known as a malignant tumor producing very poor prognosis, such drugs as melphalan, cyclophosphamide, and prednisolone are used in clinical settings. However, thus far, satisfactory therapeutic effect has not been obtained.

Myeloma tumors are formed through tumorigenesis of antibody-producing cells, and include fusion products; i.e., hybridomas, of myeloma cells and other types of cells. Typical examples of myeloma tumors include malignant tumors such as multiple myeloma and solitary plasmocytoma; and benign pathologies including immunoglobulin abnormalities, such as M-proteinemia, hypergammaglobulinemia, and Castleman's syndrome.

Among various myeloma tumors, multiple myeloma represents a malignant, uncontrolled proliferation of plasma cells derived from a single clone. In most cases of this disease, patients develop significant osteoclastic bone-resorbing lesion accompanied by intractable acute pain and risk of easy osteoclastic bone loss. Meanwhile, histopathological research of bone slices has revealed significant activation of osteoclastic cells at bone-resorbing lesions neighboring myeloma cells. From this finding, it has been considered that, in multiple myeloma, osteoclastic bone loss is caused not only by infiltration (or multiplication) of myeloma cells but also by activation of osteoclastic cells which occurs due to the osteoclast activating factor (OAF) produced by myeloma cells (N. Engl. J. Med. 1974; 29: 1041-6) (Hematol. Oncol. Clin. North Am. 1992; 6: 285-95, Br. J. Haematol. 1981; 47: 21-30).

In recent years, several cytokines, such as IL-1β (Blood 1989; 74: 380-7), lymphotoxin (TNFβ) (N. Engl. J. Med. 1987; 317: 526-32, Nature 1986; 319: 516-8), and IL-6 (J. Clin. Invest. 1989; 84: 2008-11, J. Bone Min. Res. 1991; 9: 1143-6), have been found to exhibit OAF activity. Also, in view that most myeloma tumors exhibit cytokine-dependent growth (e.g., dependent on IL-6), a substance capable of inhibiting or regulating such cytokine-dependent growth in vitro or in vivo is considered to have anti-cancer activity against myeloma tumors.

Osteopontin is a secretory phosphorylated glycoprotein, and was initially identified as a substance forming the extracellular matrix of bone. Osteopontin is expressed in a diversity of cells such as osteoclastic cells, macrophages, activated T cells, smooth muscle cells, and epithelial cells, and in some tissues such as bones, kidneys, placenta, smooth muscles, and secretory epithelium. Osteopontin has an RGD sequence (i.e., Arg-Gly-Asp sequence), and binds through αvβ1, β3, or β5 integrins in a variety of cells, to thereby induce cell adhesion, chemotaxis, and signal transmission. Osteopontin is considered to participate in normal tissue repairing processes in relation to bone resorption, angiogenesis, wound healing, and tissue injury, and also in some diseases such as restenosis, atherosclerosis, renal disorders, and tumors.

However, as described above, the myeloma tumor is quite a special tumor which only rarely responds to popular anti-cancer drugs. Therefore, components which would be effective have remained beyond expectation.

An object of the present invention is to provide preventives or remedies for myeloma tumors and osteoclastic bone loss associating therewith. Another object of the invention is to provide a screening method for candidate preventive or therapeutic drugs. A further object of the invention is to provide a method of diagnosing myeloma tumors.

DISCLOSURE OF THE INVENTION

In view of the forgoing, we carried out careful studies, and found that production of osteopontin significantly increases in a myeloma tumor; in particular, multiple myeloma. We also found that blood osteopontin level is intimately correlated with the presence of a myeloma tumor and the condition of the disease. Taking these findings together, we concluded that measurement of osteopontin level enables diagnosis of myeloma tumors; that measurement of osteopontin production regulatory or inhibitory effect enables screening of candidate preventive or therapeutic drugs for myeloma tumors; and that osteopontin production regulators or inhibitors exhibit excellent preventive or therapeutic effect against myeloma tumors and osteoclastic bone loss associated therewith, and are thus useful as pharmaceuticals for prevention or treatment of multiple myeloma, solitary plasmocytoma, M-proteinemia, hypergammaglobulinemia, or immunoglobulin disorder, and osteoclastic bone loss associated with any of these pathological conditions. The present invention has been accomplished on the basis of these findings.

Accordingly, the present invention provides a preventive or therapeutic drug for a myeloma tumor and osteoclastic bone loss associating therewith, the drug containing as an active ingredient an osteopontin-production regulator or inhibitor; a screening method for a preventive or therapeutic drug for a myeloma tumor, characterized by determining osteopontin production regulatory or inhibitory effect; as well as a diagnostic kit for a myeloma tumor, characterized by including a reagent for measuring blood osteopontin level, and a diagnostic method.

BEST MODES FOR CARRYING OUT THE INVENTION

Figure 1:
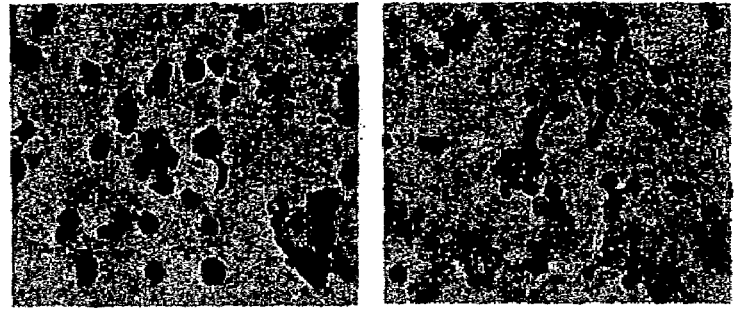
FIG. 1 shows the results of immunocytochemistry for osteopontin, performed on multiple myeloma-derived bone marrow cells (left) and cells of a control group (Monoclonal gammopaties with uncertain significance: MGUS) (right).

The preventive or therapeutic drug of the present invention for myeloma tumors and osteoclastic bone loss associating therewith contains as its active ingredient an osteopontin production regulator or inhibitor, and examples thereof include, but are not limited to, PPARγ agonists (Circ. Res. 2002; 90: 348-355) and HMG-CoA reductase inhibitors (Br. J. Pharmacol. 2001; 133: 83-88). Specific examples of PPARγ agonists include troglitazone, pioglitazone, rosiglitazone, and indomethacin; and examples of HMG-CoA reductase inhibitors include rosuvastatin, lovastatin, simvastatin, pravastatin, fluvastatin, atorvastatin, cerivastatin, pitavastatin, and mevastatin.

In use of the preventive or therapeutic drugs of the present invention for myeloma tumors and osteoclastic bone loss associating therewith, factors such as dose, site of administration, administration interval, and administration period are determined in consideration of, for example, the sex, age, body weight, and pathological condition of the patient; other drugs which may be administered in combination; and the method of therapy employed. No particular limitations are imposed on the physical form of the preventive or therapeutic drugs of the present invention for myeloma tumors and osteoclastic bone loss associating therewith. For example, the osteopontin production regulator or osteopontin production inhibitor, which serves as an active ingredient, may be used singly or in combination with other pharmacologically acceptable carriers, such as solubilizers, excipients, binders, and diluents, whereby tablets, capsules, granules, powders, lotions, ointments, injections, suppositories, etc. can be produced. These drug products may be prepared through any suitable method known per se. For example, peroral drugs may be produced by use of solubilizers such as tragacanth gum, gum arabic, sucrose esters, lecithin, olive oil, soybean oil, and PEG 400; excipients such as starch, mannitol, and lactose; binders such as carboxymethylcellulose-Na and hydroxypropylcellulose; disintegrators such as crystalline cellulose, carboxymethylcellulose-Ca; lubricants such as talc and magnesium stearate; or fluidity improvers such as light silicic acid anhydride; which may be used in suitable combinations.

The preventive or therapeutic drugs of the present invention for myeloma tumors and osteoclastic bone loss associating therewith are administered perorally or parenterally. Dose of the preventive or therapeutic drugs of the present invention for myeloma tumors and osteoclastic bone loss associating therewith differs depending on the body weight, age, sex, symptom of the patient, or other factors. For an adult, daily dose is typically 0.01 to 1000 mg, preferably 0.1 to 100 mg, which is administered in 1 to 3 divided times a day.

In the screening method of the present invention for the preventive or therapeutic drugs for myeloma tumors and osteoclastic bone loss associating therewith, osteopontin production regulatory or inhibitory effect is determined in accordance with a method known per se. For example, after a substance to be tested is added to cells having elevated osteopontin-production ability, such as myeloma cells, the osteopontin production may be measured through immunological techniques, RT-PCR, northern blotting, or western blotting. If the amount of osteopontin produced after addition of the test substance is reduced as compared with the amount determined for no addition of test substance, the substance can be determined to be effective as a preventive or therapeutic drug for myeloma tumors and osteoclastic bone loss associating therewith.

As will be shown in Examples hereinbelow, blood osteopontin level is specifically high in myeloma tumor patients. Moreover, the osteopontin level elevates as severity (stage) or activity of the disease progresses. Furthermore, patients complaining bone pain exhibit high osteopontin levels, and patients with osteoclastic bone resorption also exhibit high osteopontin levels. Therefore, measurement of blood osteopontin level enables successful diagnosis of various symptoms of myeloma tumors.

The diagnosis method of the present invention for myeloma tumors may be performed through measurement of blood osteopontin level in accordance with a conventional method.

The specimen to be used in the measurement is preferably blood, and any of whole blood, plasma, and serum may be employed. However, plasma is particularly preferred. Also, osteopontin level is preferably determined through the immunological method. In particular, use of a human osteopontin ELISA kit (Immuno-Biological Laboratories, Gunma, Japan), which will be described hereinbelow, or a similar kit is very much preferred.

The myeloma tumor diagnosing agent of the present invention should contain a reagent capable of measuring blood osteopontin level. For example, in relation to immunoassay reagents, mention may be given of a variety of reagents containing anti-osteopontin monoclonal or polyclonal antibodies. Specifically, a human osteopontin ELISA kit or a similar kit is particularly preferred.

EXAMPLES

The present invention will next be described in more detail by way of examples, which should not be construed as limiting the invention thereto.

Example 1

Imunocytochemistry for Osteopontin

Expression of osteopontin in bone marrow cells collected from three patients suffering typical multiple myeloma was studied through an imunocytochemical technique employing the avidin-biotin-peroxidase complex method. The control group employed consisted of bone marrow cells collected from five patients suffering blood disease (including MGUS) but not multiple myeloma. Here, "MGUS" stands for monoclonal gammopaties with uncertain significance, which is a pathological condition in which despite elevation of monoclonal immunoglobulin being observed, other criteria for rendering diagnosis of multiple myeloma are not met. Bone marrow cells were isolated through density-gradient centrifugation. From each patient, $1 \times 10^5$ bone marrow cells were collected, and the cells were secured onto glass slide with Cytospin 2 (Shandon Soutern Products Ltd., Cheshire, UK). The thus-prepared slide was stored at −80° C. until use. The primary antibody employed was mouse anti-human osteopontin monoclonal IgG antibody (4C1) created by Kon and his colleagues (J. Cellular Biochemistry 2002; 84: 420-432). As a negative control, mouse IgG antibody (Pharmingen, San Diego, USA), which was irrelevant to osteopontin, was used at the same concentration as a primary antibody. Biotinylated horse anti-mouse IgG antibody (Vector Laboratories, Burlingame, USA) was used as the second antibody. The slides that had undergone treatment with Cytospin was immersed in cold isopropanol for 2 minutes, whereby the cells were fixed. 10% Normal horse serum was used for blocking, followed by reaction overnight at 4° C. by use of 4C1 or the negative control antibody. Intrinsic peroxidase activity was inhibited through 30-minute treatment with 0.3% hydrogen peroxidase methanol solution. Washing was performed with PBS (phosphate buffer), and thereafter, reaction was allowed to proceed at room temperature for 2 hours with biotinylated secondary antibody. Washing was performed again, and avidin-horseradish peroxidase complex (VECTASTAIN Elite ABC kit, Vector Laboratories, Burlingame, USA) was allowed to react therewith for one hour. Subsequently, color was allowed to develop by use of a substrate incorporating diaminobenzene tetrahydrochloride (DBA). Also, Giemsa staining was performed for counting cells.

As a result, as shown in FIG. 1, most bone marrow cells which exhibited typical form of myeloma cells were stained brown with 4C1, which is a mouse anti-human osteopontin monoclonal IgG antibody (left photo), whereas no development of color was observed for control antibody (right photo).

Figure 2:
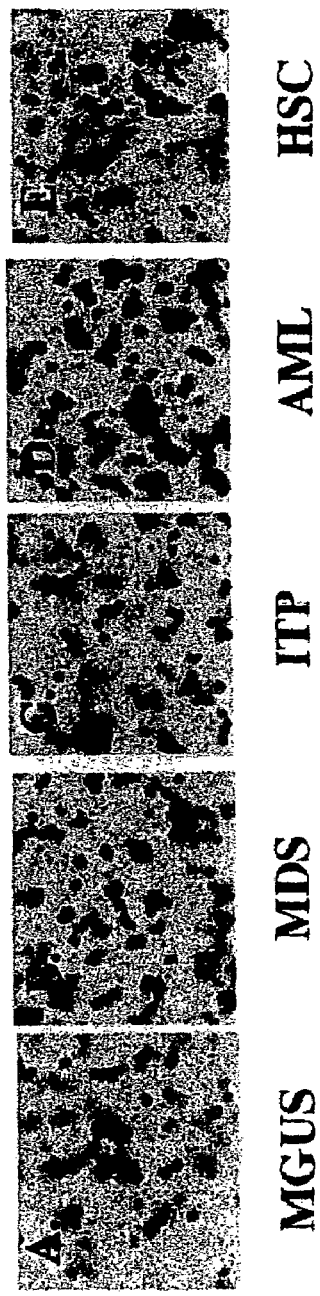
FIG. 2 shows the results of immunocytochemistry for osteopontin, performed on MGUS (A), myelodysplastic syndrome (MDS) (B), idiopathic thrombocytopenic purpura (ITP) (C), acute myeloid leukemia (AML) (D), and hereditary spherocytosis (HSC) (E).

Also, as shown in FIG. 2, in any of bone marrow cells derived from MGUS (photo A), myelodysplastic syndrome (photo B), idiopathic thrombocytopenic purpura (photo C), acute myeloid leukemia (photo D), or hereditary spherocytosis (photo E), stains proving expression of osteopontin could not be observed.

Accordingly, osteopontin has been found to be specifically expressed in myeloma cells.

Example 2

Reverse Transcription Polymerase Chain Reaction (RT-PCR) Analysis for Osteopontin mRNA expression of osteopontin was studied using B cells of different stages. The employed cells were RPMI 8226 (myeloma cell line); Daudi (Burkitt's lymphoma-derived lymphoblast-like B cell line); Ramos (Burkitt's lymphoma-derived lymphoblast B cell line); Raji (Burkitt's lymphoma-derived lymphoblast B cell line); Kopn-8 (pre-B cell line); NALM-16 (pro-B cell line); and Reh (pro-B cell line). The study employed human osteopontin-based specific primers (sense primer; 5'-GGACTCCATT GACTCGAACG-3' (SEQ ID NO: 1) and antisense primer; 5'-TAATCTGGACTGCT-TGTGGC-3' (SEQ ID NO: 2)), and RT-PCR was performed. From each of the above cell lines, mRNA (100 ng) was prepared and purified by use of a TRIZOL reagent (Life Technologies, Rockville, USA), following by the synthesis of cDNA. The conditions under which PCR was performed by use of osteopontin-specific primers were as follows: Once cycle consisted of denaturation at 94° C. for 1 minute, annealing at 57° C. for 1 minute, and elongation at 72° C. for 2 minutes, and this cycle was repeated 30 times. As a control, primers specific to GAPDH (Glyceraldehyde-3-phosphate dehydrogenase) (a sense primer 5'-AATTACCACAAC-CCCTACAAAC-3' (SEQ ID NO: 3) and an antisense primer 5'-CAACTCTGCAACATCTTCCTC-3' (SEQ ID NO: 4)) were employed. The PCR products were electrophoresed on 2% agarose gel for checking the presence or absence of band.

Figure 3:
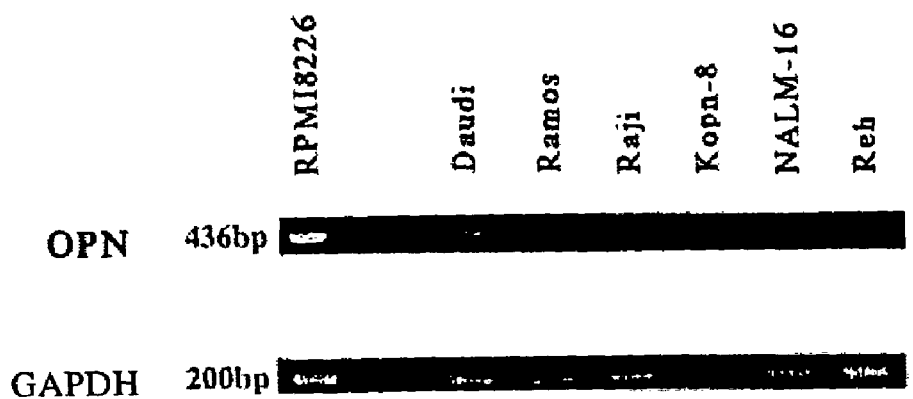
FIG. 3 shows expression of osteopontin (OPN) and GAPDH in a variety of cell lines, obtained from RT-PCR.

As a result, as shown in FIG. 3, RPMI 8226 (myeloma cell line) exhibited a clear band, and Daudi also exhibited a weak band. However, cell lines other than the myeloma cell line produced no band attributed to osteopontin.

Example 3

Western-Blotting Analysis for Osteopontin

In order to study spontaneous osteopontin production, western blotting analysis was performed by use of similar B cell line as employed in Example 2 but collected from different stages. The cells were cultured in vitro for three days and the supernatant was collected. From a 20 µL aliquot of the supernatant of each cell sample, protein was separated by SDS-PAGE on 4-20% acrylamide density-gradient gel, performed for 4 hours. The protein was transferred onto an Immobilon P membrane (Millipore, Bedford, USA) at 4° C. overnight. The membrane to which the protein had been transferred was blocked with 10% skim milk and phosphate buffer containing 0.1% Tween 20. The membrane was washed, and then reacted with rabbit anti-human osteopontin antibody (OPN-2) (J Cell Biochem. 2000; 77: 487-498) created by Kon and his colleagues at 4° C. overnight. After washing, HRP-labeled goat anti-rabbit IgG antibody was added for reaction at room temperature for one hour. Washing was performed again, and film was sensitized overnight with a Renaissance reagent (NEN Life Science Products, Boston, USA), whereby signals were detected.

Figure 4:
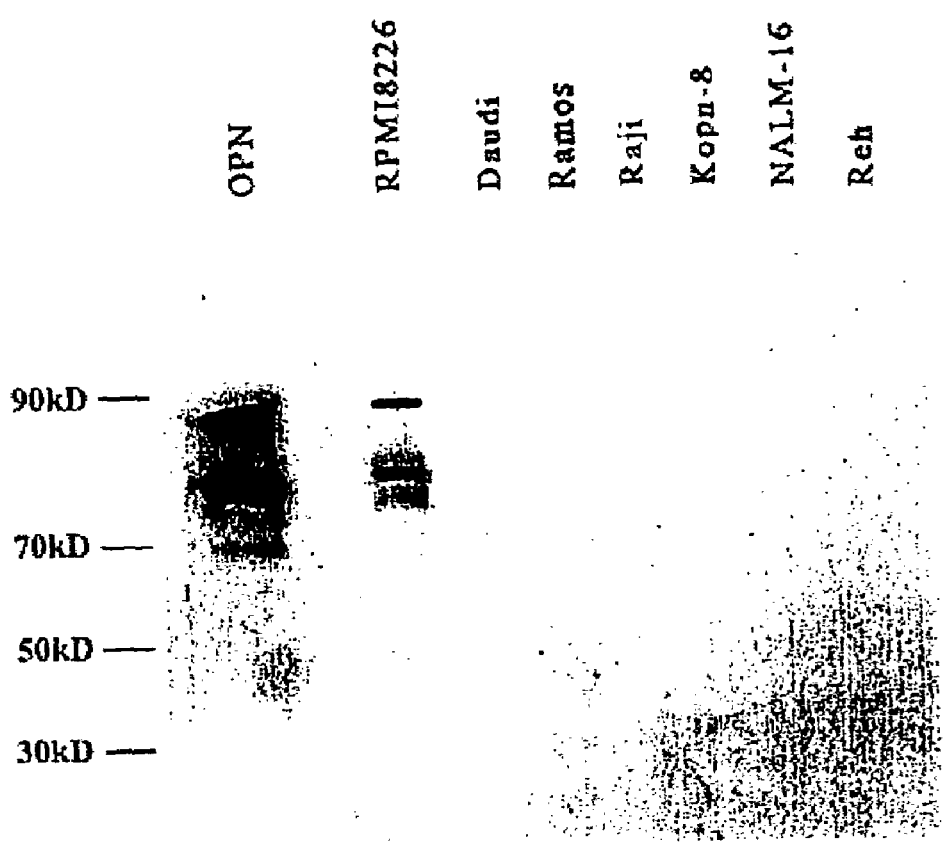
FIG. 4 shows expression of osteopontin (OPN) in a variety of cells, obtained from western blotting.

As is apparent from FIG. 4, bands attributed to osteopontin were observed only for RPMI 8226, and no bands were observed for other cells.

FIGS. 3 and 4 show that osteopontin is expressed specifically in myeloma cells, but not in other tumor cell lines.

Example 4

Enzymed Linked Immunosorbent Assay for Osteopontin

Plasma osteopontin level was measured for 30 multiple myeloma patients by use of a human osteopontin ELISA kit (Immuno-Biological Laboratories, Gunma, Japan). Plasma samples from 21 MGUS patients and 30 healthy volunteers were employed as control samples. Data are represented by mean±standard error. The Mann-Whitney U Test was performed. When the P value is smaller than 0.05; i.e., when the level of significance is lower than 5%, a statistically significant difference is considered to be present.

Figure 5:
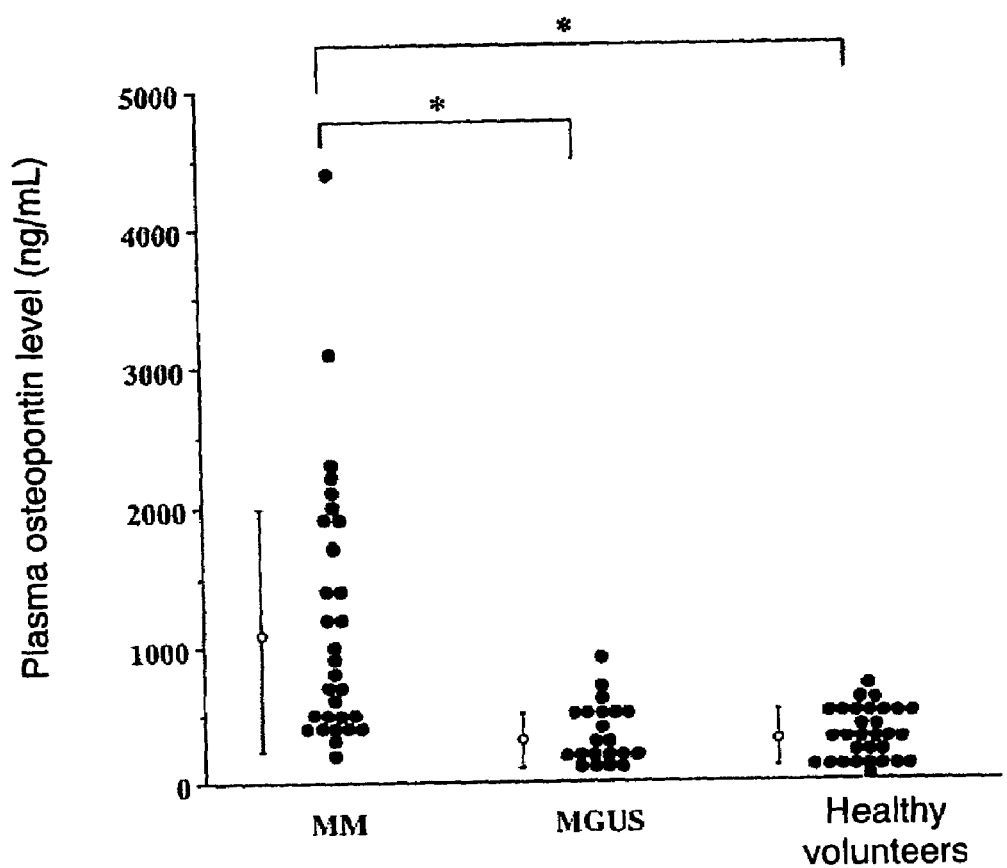
FIG. 5 shows the distributions of plasma osteopontin level in multiple myeloma patients (MM), MGUS, and healthy volunteers.

As is apparent from FIG. 5, the plasma osteopontin levels of multiple myeloma patients are significantly higher than those of MGUS patients and healthy volunteers.

Plasma osteopontin levels (mean±standard error); multiple myeloma 1053±957 ng/mL, MGUS 355±205 ng/mL, healthy volunteers 309±184 ng/mL.

Multiple myeloma versus MGUS patients or healthy volunteers; *$p<0.05$.

Figure 6:
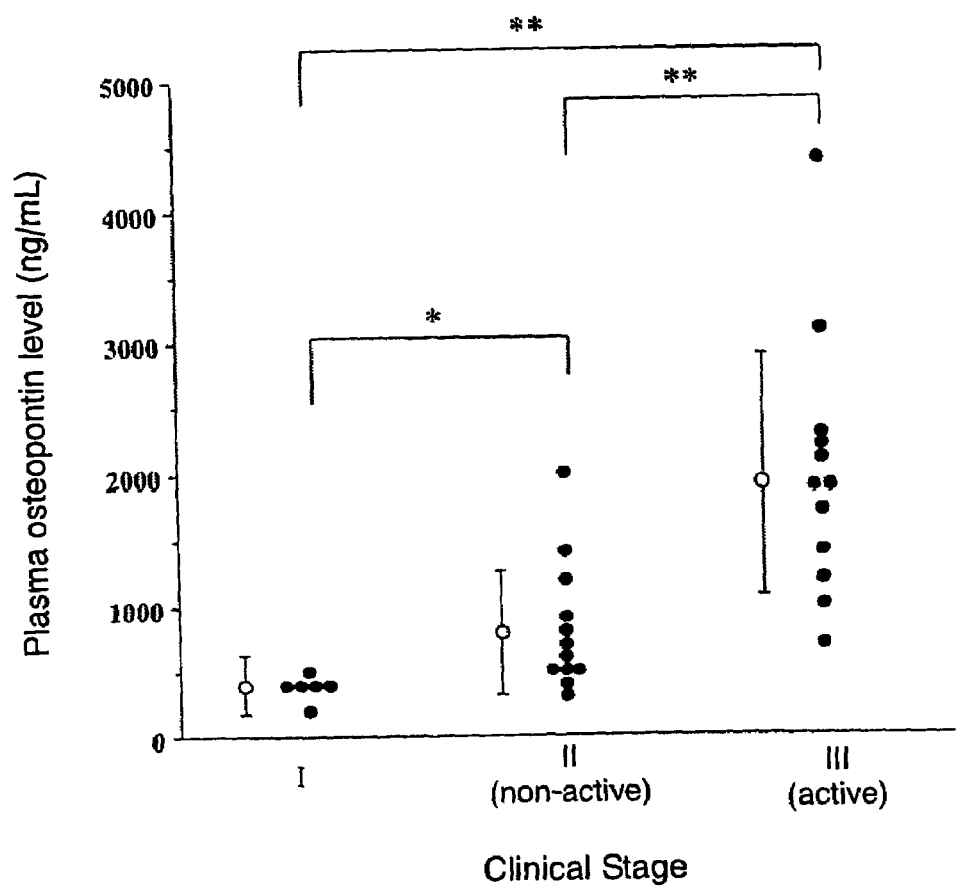
FIG. 6 shows plasma osteopontin levels of stage I, stage II (non-active), and stage III (active) multiple myeloma patients.

FIG. 6 shows the results obtained from comparison of plasma osteopontin levels of multiple myeloma patients classified into three stages; i.e., Stage I (6 patients), Stage II (non-active) (12 patients), and Stage III (active) (12 patients), according to the Durie & Salmon staging system (Cancer 1975; 36: 842-54). As is apparent form FIG. 6, the plasma osteopontin levels of multiple myeloma patients showed significant stage- or activity-dependent increases.

Plasma osteopontin levels (mean±standard error); Stage I 389±89 ng/mL, Stage II (non-active) 816±446 ng/mL, Stage III (active) 1991±953 ng/mL.

Stage II (non-active) versus Stage I: *p<0.05
Stage III (active) versus Stage I or Stage II (non-active): *p<0.05.

Figure 7:
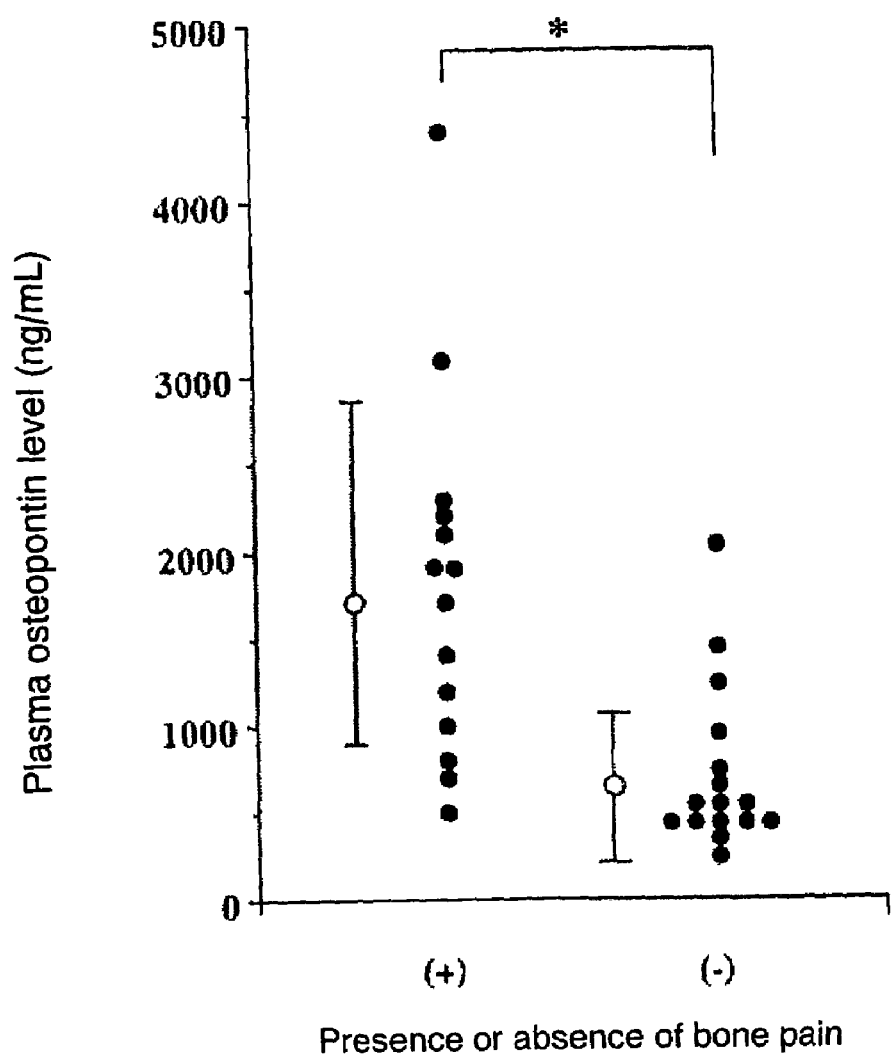
FIG. 7 shows the difference in terms of plasma osteopontin level of multiple myeloma patients grouped on the basis of the presence or absence of bone pain.

FIG. 7 shows the result of comparison of plasma osteopontin levels between two groups of multiple myeloma patients. One group consisted of patients having almost no bone pain, and the other group consisted of patients complaining severe bone pain. The plasma osteopontin levels of the patients having severe bone pain were significantly higher than those of the patients having little bone pain.

Plasma osteopontin levels (mean±standard error); bone pain [−] 776±660 ng/mL, bone pain [+] 1822±994 ng/mL.

bone pain [+] versus bone pain [−]; *p<0.05.

Figure 8:
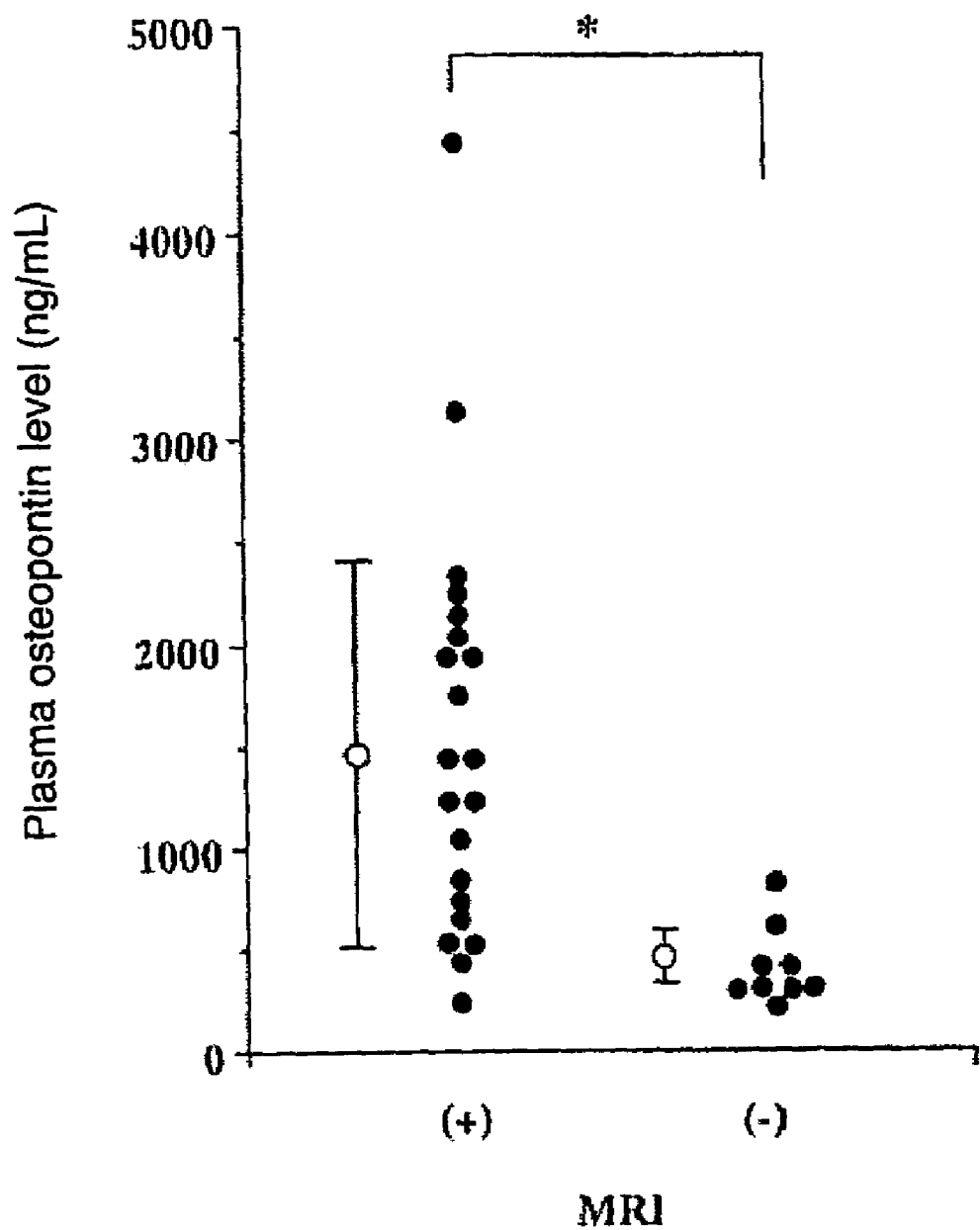
FIG. 8 shows the difference in terms of plasma osteopontin level of multiple myeloma patients grouped on the basis of the presence or absence of an image substantiating osteoclastic bone-resorbing lesions.

FIG. 8 shows the results of comparison of plasma osteopontin levels between two groups of multiple myeloma patients. One group consisted of patients who had provided images of almost no osteoclastic bone-resorbing lesions through magnetic resonance imaging (MRI). Another group consisted of patients who had provided clear images of osteoclastic bone-resorbing lesions. The plasma osteopontin levels of patients in the group of clear osteoclastic bone-resorbing lesions were significantly higher than those of patients in the group of almost no osteoclastic bone-resorbing lesion.

Plasma osteopontin levels (mean±standard error); osteoclastic bone-resorbing lesions [−] 486±169 ng/mL, osteoclastic bone-resorbing lesions [+] 1498±486 ng/mL.

osteoclastic bone-resorbing lesions [+] versus osteoclastic bone-resorbing lesions [−]; *p<0.05.

INDUSTRIAL APPLICABILITY

The present invention enables diagnosis of not only the presence of a myeloma tumor, which is an intractable, malignant tumor producing poor prognosis, but also the severity of the disease. According to the present invention, preventive or therapeutic drugs for myeloma tumors and osteoclastic bone loss associated therewith as well as a screening method for such drugs are provided.

The invention claimed is:

1. A method for identifying a compound that reduces the severity of myeloma comprising:

contacting cells which produce osteopontin with a test compound and determining the amount of osteopontin produced in the presence of said test compound compared to the amount of osteopontin produced by the cells in the absence of said test compound, selecting a test compound which reduces the amount of osteopontin produced by said cells, and contacting said test compound, which reduces the amount of osteopontin produced, with myeloma tumor cells, and selecting a test compound which reduces the severity of myeloma.

2. The method of claim 1, wherein said cells which produce osteopontin are B-cells or a B-cell line.

3. The method of claim 1, which is an in vitro method.

4. The method of claim 1, wherein the ability of the test compound to reduce osteopontin production is determined by ELISA.

5. The method of claim 1, wherein the ability of the test compound to reduce osteopontin production is determined by an immunological technique.

6. The method of claim 1, wherein the ability of the test compound to reduce osteopontin production is determined by Western blotting.

7. The method of claim 1, wherein the ability of the test compound to reduce osteopontin production is determined by RT-PCR.

8. The method of claim 1, wherein the ability of the test compound to reduce osteopontin production is determined by northern blotting.

9. The method of claim 1, wherein said test compound which reduces osteopontin level is selected based on its ability to reduce bone pain in a subject having myeloma.

10. The method of claim 1, wherein said test compound which reduces osteopontin level is selected based on its ability to reduce the number of osteoclastic bone-resorbing lesions in a subject having myeloma.

* * * * *